US009434829B2

(12) United States Patent
Rasmussen et al.

(10) Patent No.: US 9,434,829 B2
(45) Date of Patent: Sep. 6, 2016

(54) LIGAND GRAFTED SUBSTRATES

(71) Applicant: 3M INNOVATIVE PROPERTIES COMPANY, St. Paul, MN (US)

(72) Inventors: Jerald K. Rasmussen, Woodville, WI (US); Catherine A. Bothof, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/415,862

(22) PCT Filed: Sep. 23, 2013

(86) PCT No.: PCT/US2013/061111
§ 371 (c)(1),
(2) Date: Jan. 20, 2015

(87) PCT Pub. No.: WO2014/052215
PCT Pub. Date: Apr. 3, 2014

(65) Prior Publication Data
US 2015/0203645 A1     Jul. 23, 2015

Related U.S. Application Data

(60) Provisional application No. 61/706,288, filed on Sep. 27, 2012.

(51) Int. Cl.
| *C08J 7/18* | (2006.01) |
| *B01J 20/26* | (2006.01) |
| *B01J 20/289* | (2006.01) |
| *B01J 20/32* | (2006.01) |
| *G01N 33/543* | (2006.01) |
| *C08J 7/04* | (2006.01) |
| *C09D 179/02* | (2006.01) |
| *C08G 73/02* | (2006.01) |
| *C07K 1/22* | (2006.01) |
| *C07K 14/765* | (2006.01) |
| *C07K 16/00* | (2006.01) |

(52) U.S. Cl.
CPC ............. *C08J 7/18* (2013.01); *B01J 20/267* (2013.01); *B01J 20/289* (2013.01); *B01J 20/327* (2013.01); *B01J 20/3212* (2013.01); *B01J 20/3219* (2013.01); *B01J 20/3276* (2013.01); *B01J 20/3278* (2013.01); *B01J 20/3282* (2013.01); *C07K 1/22* (2013.01); *C07K 14/765* (2013.01); *C07K 16/00* (2013.01); *C08G 73/02* (2013.01); *C08J 7/047* (2013.01); *C09D 179/02* (2013.01); *G01N 33/54393* (2013.01); *C08J 2333/24* (2013.01); *C08J 2377/06* (2013.01); *C08J 2433/14* (2013.01)

(58) Field of Classification Search
None
See application file for complete search history.

(56) References Cited

U.S. PATENT DOCUMENTS

| 3,583,950 | A | | 6/1971 | Kollinsky |
| 3,876,738 | A | | 4/1975 | Marinaccio |
| 3,928,517 | A | | 12/1975 | Knight |
| 4,157,418 | A | | 6/1979 | Heilmann |
| 4,304,705 | A | | 12/1981 | Heilmann |
| 4,352,884 | A | | 10/1982 | Nakashima |
| 4,529,256 | A | | 7/1985 | Kretzschmar |
| 4,707,265 | A | | 11/1987 | Barnes, Jr. |
| 4,726,989 | A | | 2/1988 | Mrozinski |
| 4,867,881 | A | | 9/1989 | Kinzer |
| 5,039,549 | A | | 8/1991 | Nguyen |
| 5,120,594 | A | | 6/1992 | Mrozinski |
| 5,260,360 | A | | 11/1993 | Mrozinski |
| 5,344,701 | A | * | 9/1994 | Gagnon ............. A61L 33/0011 428/304.4 |
| 5,458,782 | A | | 10/1995 | Hou |
| 5,506,279 | A | | 4/1996 | Babu |
| 5,902,836 | A | | 5/1999 | Bennett |
| 5,962,544 | A | | 10/1999 | Waller, Jr. |
| 6,056,529 | A | | 5/2000 | Meyering |
| 6,096,369 | A | * | 8/2000 | Anders ...................... C08J 7/16 427/2.28 |
| 6,150,103 | A | | 11/2000 | Ness |
| 6,267,916 | B1 | | 7/2001 | Meyering |
| 6,413,070 | B1 | | 7/2002 | Meyering |
| 6,776,940 | B2 | | 8/2004 | Meyering |
| 6,794,458 | B2 | | 9/2004 | Haddad |
| 7,125,603 | B2 | | 10/2006 | David |
| 7,338,692 | B2 | | 3/2008 | Smith |
| 2008/0009078 | A1 | | 1/2008 | O'Neill |
| 2012/0252091 | A1 | | 10/2012 | Rasmussen |

FOREIGN PATENT DOCUMENTS

| EP | 0490854 | 6/1992 |
| WO | WO 96-37241 | 11/1996 |
| WO | WO 97-02313 | 1/1997 |
| WO | WO 2009-146321 | 12/2009 |
| WO | WO 2009-148869 | 12/2009 |
| WO | WO 2009148869 A1 * | 12/2009 ............ B01J 20/285 |
| WO | WO 2010-033794 | 3/2010 |

(Continued)

OTHER PUBLICATIONS

Laible, "Formation of chemically bound polymer layers on oxide surfaces and their role in colloidal stability", Advances in Colloid and Interface Science, 1980, vol. 13, pp. 65-99.

(Continued)

*Primary Examiner* — Satya Sastri

(74) *Attorney, Agent, or Firm* — Kent S. Kokko

(57) ABSTRACT

Ligand-functionalized substrates are describe that are useful in selectively binding and removing biological materials from biological samples, and methods for preparing the same.

16 Claims, No Drawings

(56) References Cited

FOREIGN PATENT DOCUMENTS

| WO | WO 2011-103106 | 8/2011 | | |
|---|---|---|---|---|
| WO | WO 2012-134636 | 10/2012 | | |
| WO | WO 2012134636 A1 | * 10/2012 | ......... | B01D 67/0093 |

OTHER PUBLICATIONS

Oster, "Ultraviolet Induced Crosslinking and Grafting of Solid High Polymers", Journal of Polymer Science, 1959, vol. 34, pp. 671-684.
Prucker, "Microstructuring of Molecularly Thin Polymer Layers by Photolithography", Advanced Materials, 1998, vol. 10, No. 14, pp. 1073-1077.
Ranby, "Modification of Polymer Surfaces by Photoinduced Graft Copolymerization", American Chemical Society, 1988, pp. 170-186.
Rohr, "Surface Functionalization of Thermoplastic Polymers for the Fabrication of Microfluidic Devices by Photoinitiated Grafting", Advanced Functional Materials, 2003, vol. 13, No. 4, pp. 264-270.
Smith, Introduction to Chemical Engineering Thermodynamics, 308-313, (1959).
Tasdelen, "Poly(propylene imine) dendrimers as hydrogen donor in Type II photoinitiated free radical polymerization", European Polymer Journal, 2007, vol. 43, pp. 4423-4430.
Towns, "Polyethyleneimine-bonded phases in the separation of proteins by capillary electrophoresis", Journal of Chromatography A, 1990, vol. 516, pp. 69-78.
Wang, "Influence of pore structure and architecture of photo-grafted functional layers on separation performance of cellulose-based macroporous membrane adsorbers", Journal of Chromatography A, 2009, vol. 1216, pp. 6490-6501.
International Search Report for PCT International Application No. PCT/US2013/061111, mailed on Jan. 20, 2014, 4pgs.

* cited by examiner

LIGAND GRAFTED SUBSTRATES

CROSS REFERENCE TO RELATED APPLICATIONS

This application is a national stage filing under 35 U.S.C. 371 of PCT/US2013/061111, filed Sep. 23, 2013, which claims priority to Provisional Application No. 61/706,288, filed Sep. 27, 2012, the disclosure of which is incorporated by reference in its/their entirety herein.

TECHNICAL FIELD

The present disclosure relates to ligand-grafted substrates, and methods for preparing the same. The graft-functionalized substrates are useful in selectively binding and removing biological materials, such as proteins, from biological samples.

BACKGROUND

Detection, quantification, isolation and purification of target biomaterials, such as microbes and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biological targets are important for therapeutic uses and in biomedical research. Biomolecules such as enzymes which are a special class of proteins capable of catalyzing chemical reactions are also useful industrially.

In their native state in vivo, structures and corresponding biological activities of biomolecules are maintained generally within fairly narrow ranges of pH and ionic strength. Consequently, any separation and purification operation must take such factors into account in order for the resultant, processed biomacromolecule to have potency.

Chromatographic separation and purification operations have become the primary method for the isolation of biological molecules in the biopharmaceutical industry. Most current chromatography is done via conventional column techniques, and are operated in either bind-and-elute (e.g., when the target species is the object of purification) or in flow-through mode (e.g., when the target species if a contaminant to be removed). These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the adsorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Membrane chromatography has the potential to offer significant advantages over column chromatography for the separation of biomaterials, especially biomolecules, due to the convective nature of the fluid flow through the material. With the polymeric resins widely used for column chromatography, pore diffusion must also occur in order for the target molecule to interact with its binding site, dramatically increasing the processing time needed for the separation operation. The main problems with utilization of membrane chromatography for large-scale purifications, however, have been the lack of good techniques for functionalization of the membranes and generally the low binding capacities for target species. Thus, there is a need in the art for polymeric substrates, especially membranes, having enhanced affinity for microbes and other biological species to allow selective removal from a biological sample. There is further need in the art for ligand functionalized substrates that overcome limitations in diffusion and binding, and that may be operated at high throughput and at lower pressure drops.

SUMMARY OF THE INVENTION

The present disclosure is directed to ligand-functionalized polymers, methods of making the same, and substrates bearing a grafted coating of the ligand-functional polymers. More specifically, the substrate comprises a crosslinked copolymer layer, and grafted thereto a ligand-functional polymer. The grafted ligand functional copolymer coating comprises the UV reaction product of:

1) a crosslinked copolymer, the copolymer comprising photoinitiator-functional monomer units, and monomer units amenable to crosslinking reactions (such as, monomer units having an amine-reactive functional group); and 2) a monomer mixture comprising ligand-functional monomer units.

The ligand-grafted copolymer has the requisite affinity for binding near neutral or charged biomaterials, such as cells, cell debris, bacteria, spores, viruses, nucleic acids, polysaccharides, lipids, and proteins. The type of binding and the biomaterials bound will vary, depending upon the type of ligand present on the ligand-functional monomer.

"Affinity" means the ability to bind biological species by any means, including ionic, covalent, hydrophobic, and biological affinity (such as antibody-antigen) interactions.

"Alkyl" means a linear or branched, cyclic or acyclic, saturated monovalent hydrocarbon having from one to about twelve carbon atoms, e.g., methyl, ethyl, 1-propyl, 2-propyl, pentyl, and the like.

"Alkylene" means a linear saturated divalent hydrocarbon having from one to about twelve carbon atoms or a branched saturated divalent hydrocarbon having from three to about twelve carbon atoms, e.g., methylene, ethylene, propylene, 2-methylpropylene, pentylene, hexylene, and the like.

"Alkenyl" means a linear unsaturated monovalent hydrocarbon having from two to about twelve carbon atoms or a branched unsaturated hydrocarbon having from three to about twelve carbon atoms.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

"Heteroarylene" refers to a divalent group that is aromatic and heterocyclic. That is, the heteroarylene includes at least one heteroatom in an aromatic ring having 5 or 6 members. Suitable heteroatoms are typically oxy, thio, or amino. The group can have one to five rings that are connected, fused, or a combination thereof. At least one ring is heteroaromatic and any other ring can be aromatic, non-aromatic, heterocyclic, carbocyclic, or a combination thereof. In some embodiments, the heteroarylene has up to 5 rings, up to 4 rings, up to 3 rings, up to 2 rings, or one ring. Examples of heteroarylene groups include, but are not limited to, triazine-diyl, pyridine-diyl, pyrimidine-diyl, pyridazine-diyl, and the like.

"hydrocarbyl" is inclusive of aryl and alkyl;

"(Hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"(Hetero)arylene" is inclusive of arylene and heteroarylene.

DETAILED DESCRIPTION

In the article and methods of this invention, ligand-functionalized substrates are provided which have enhanced affinity and/or capacity for biological materials, such as proteins, DNA, RNA, polysaccharides, lipids, viruses, and other microorganisms. The ligand functionalized substrate allows the selective capture or binding of target biomaterials by the ligand groups, while other materials, lacking the affinity for the ligand groups, are passed.

The copolymer comprises polymerized monomer units of grafting photoinitiator monomers, which includes ethylenically unsaturated, polymerizable groups, including (meth)acryloyl groups and alkenyl groups, and an α-cleavage-type photoinitiator group, and may be represented by the formula:

$$\underset{R^1}{\overset{O}{\underset{\|}{\text{=}}}}-X^1-R^6-PI \qquad I$$

where;

$X^1$ is —O— or —NR$^1$, $R^1$ is independently H or $C_1$-$C_4$ alkyl;

$R^6$ is a divalent (hetero)hydrocarbyl linking group connecting the (meth)acryloyl group with the photoinitiator group; and PI is a α-cleavage photoinitiator group represented by the structure:

$$-\underset{R^{12}}{\text{Ar}}-\overset{O}{\underset{\|}{C}}-R^{13} \qquad II$$

in which Ar is a substituted arene having 6 to 12 carbon atoms, preferably a benzenetriyl group;

$R^{12}$ is hydrogen, a $C_1$ to $C_{12}$ alkyl group, a $C_1$ to $C_{12}$ alkoxy group, or a phenyl group; and $R^{13}$ is selected from the groups consisting of:

$$\begin{array}{c} R^{16} \\ | \\ \text{---}\!\!\!\!-\text{---}R^{17} \\ | \\ R^{18} \end{array}$$

[piperidine ring with $R^{19}$ substituent, N-H]

[piperazine-type ring with $R^{19}$]

[morpholine-type ring with O and $R^{19}$]

in which $R^{19}$ is hydrogen, a $C_1$ to $C_{12}$ alkyl group, a $C_1$ to $C_{12}$ alkoxy group, or a phenyl group, $R^{16}$, $R^{17}$, and $R^{18}$ are independently a hydroxyl group, a phenyl group, a $C_1$ to $C_6$ alkyl group, a $C_1$ to $C_6$ alkoxy group, or a —NR$^{19}$R$^{20}$ group, wherein $R^{19}$ and $R^{20}$ are independently hydrogen or a $C_1$ to $C_{12}$ alkyl group, with the proviso that, when $R^{13}$ is —CR$^{16}$R$^{17}$R$^{18}$, one of the following must be true:

(1) at least one of $R^{16}$, $R^{17}$, and $R^{18}$ is selected from the class consisting of hydroxyl, alkoxy, and —NR$^{19}$R$^{20}$ groups;

(2) any two of $R^{16}$, $R^{17}$, and $R^{18}$ together are one of —C$_t$H$_{2t}$— and —C$_t$H$_{2t}$O— wherein t is either 2 or 3 so that they, together with the carbon atoms to which they are attached, form a 5- or 6-membered ring; and (3) any two of $R^{16}$, $R^{17}$, and $R^{18}$ together are a carbonyl group, provided that the remaining one of $R^{16}$, $R^{17}$, and $R^{18}$ is selected from the class consisting of hydroxy, alkoxy, —NR$^{19}$R$^{20}$, and phenyl groups.

In certain preferred embodiments, the photoinitiator monomers may be of the α-cleavage type represented by the general formula:

$$\underset{R^1}{\overset{O}{\underset{\|}{\text{=}}}}\!\!-\!\!\left[\text{---}X^1\text{---}[(M^1)_a\text{---}(M^2)_b\text{---}(M^3)_c]_o\right]_p\text{---}G\text{---}PI \qquad IV$$

$X^1$ is O or NR$^1$;

p is 0 or 1;

o is 0 or an integer from 1 to 5;

a, b, and c are independently 0 or 1;

$M^1$ is CH$_2$ or Si(R$^1$)$_2$;

$M^2$ is C(R$^1$)$_2$ or Si(R$^1$)$_2$;

$M^3$ is —O—, —NH—, —C(O)—, —C(O)O—, —C(O)NH—, or —OC(O)NH—;

Each $R^1$ is independently H or a $C_1$ to $C_4$ alkyl group;

G is a covalent bond, —(CH$_2$)$_d$—, or —(CH$_2$)$_d$O— where d is an integer from 1 to 4, preferably from 1 to 2;

PI is an α-cleavage type photoinitiator group.

Such photoinitiator monomers are described, for example, in U.S. Pat. No. 5,902,836 (Bennett, et al.) and U.S. Pat. No. 5,506,279 (Babu et al.), the disclosures of which are herein incorporated by reference. Further details regarding the linking $R^6$ group may be found with reference to the method of preparing the photoinitiator grafting monomer herein, and in the cited references. A particularly useful polymerizable photoinitiator is the one:one adduct of 2-vinyl-4,4-dimethylazlactone with Irgacure™ 2959, prepared as disclosed in Example 1 of U.S. Pat. No. 5,506,279 (Babu et al.), incorporated herein by reference.

A variety of photoinitiator-functional grafting monomers can be made by reaction of: 1) an acryloyl or alkenyl monomer comprising a first reactive functional group with 2) a compound that comprises a radiation-sensitive group (photoinitiator group) and a second reactive functional group, the two functional groups being co-reactive with each other. When the first and second functional groups react, they form a covalent bond and link the co-reactive compounds.

Examples of useful reactive functional groups include hydroxyl, amino, oxazolinyl, oxazolonyl, acetyl, acetonyl, carboxyl, isocyanato, epoxy, aziridinyl, acyl halide, and cyclic anhydride groups. Where the first reactive functional group is an isocyanato functional group, the second, co-reactive functional group preferably comprises a amino, carboxyl, or hydroxyl group. Where the first reactive functional group comprises a hydroxyl group, the second, co-reactive functional group preferably comprises a carboxyl, isocyanato, epoxy, anhydride, acyl halide, or oxazolinyl group. Where the first reactive functional group comprises a carboxyl group, the second co-reactive functional group preferably comprises a hydroxyl, amino, epoxy, vinyloxy, or oxazolinyl group.

Representative examples of acrylate compounds having a reactive functional group include hydroxyalkyl acrylates such as 2-hydroxyethyl acrylate and 2-(2-hydroxyethoxy)ethyl acrylate; aminoalkyl acrylates such as 3-aminopropyl acrylate; oxazolonyl compounds such as 2-ethenyl-1,3-oxazolin-5-one and 2-propenyl-4,4-dimethyl-1,3-oxazolin-5-one; carboxy-substituted compounds such as acrylic acid and 4-carboxybenzyl acrylate; isocyanato-substituted compounds such as isocyanatoethyl acrylate and 4-isocyanatocyclohexyl acrylate; epoxy-substituted compounds such as glycidyl acrylate; aziridinyl-substituted compounds such as N-acryloylaziridine; and acryloyl halides.

Representative examples of co-reactive compounds include functional group-substituted compounds such as 1-(4-hydroxyphenyl)-2,2-dimethoxyethanone, 1-[4-(2-hydroxyethyl)phenyl]-2,2-dimethoxyethanone, (4-isocyanatophenyl)-2,2-dimethoxy-2-phenylethanone, 1-{4-[2-(2,3-epoxypropoxy)phenyl]}-2,2-dimethyl-2-hydroxyethanone, 1-[4-(2-aminoethoxy)phenyl]-2,2-dimethoxyethanone, and 1-[4-(carbomethoxy)phenyl]-2,2-dimethoxyethanone.

The weight percentage of the photoinitiator monomers of Formula I or IV in the copolymer(s) may be at least about 0.5%, and generally less than about 25%, relative to the total weight of monomers of the copolymer. Those photoinitiator monomers incorporated into the copolymer chain will, on exposure to UV radiation, initiate free radical polymerization of the ligand monomers and incorporate the same as grafted chains onto the crosslinked copolymer.

The copolymer comprises monomer units amenable to crosslinking reactions—"crosslinkable monomer units". Inclusion of such monomers allows application of a cross-linked coating containing a copolymerized photoinitiator monomer onto a variety of substrates. Such monomers are well known in the art, and include such monomers as alkenyl and (meth)acryloylalkyl silanes, hydroxymethyl and alkoxymethyl(meth)acrylamides, and monomers containing amine-reactive functional groups. The latter monomers are especially preferred since they allow coating and crosslinking operations to be conducted at low temperatures, such as at room temperature.

The crosslinkable monomer units of the copolymer have a polymerizable, ethylenically unsaturated group and a reactive functional group capable of crosslinking, some embodiments of which are of the formula V:

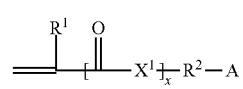

wherein
$X^1$ is —O— or —$NR^1$—,
$R^1$ is H or $C_1$-$C_4$ alkyl;
$R^2$ is a single bond or a (hetero)hydrocarbyl linking group, preferably divalent alkylene of 1 to 20 carbon atoms;
A is an reactive functional group that is reactive with the crosslinking compound or is self-crosslinking, including mono-, di-, or trialkoxysilane, and hydroxymethyl- or alkoxymethy-substituted nitrogen; and
x is 0 or 1.

In some embodiments compounds of Formula V are (meth)acryloyl compounds, and in other embodiments are alkenyl compounds. Preferably "A" is an amine-reactive functional group. Preferably, $R^2$ is a single bond or a hydrocarbyl linking group that joins an ethylenically unsaturated, polymerizable group (e.g. alkenyl or (meth)acryl group) to reactive functional group A and preferably is an alkylene group having 1 to 6 carbon atoms, a 5- or 6-membered cycloalkylene group having 5 to 10 carbon atoms, or a divalent aromatic group having 6 to 16 carbon atoms; and A is a reactive functional group capable of reacting with an amine group of the crosslinking agent.

Useful amine-reactive functional groups "A" include carboxyl, oxazolinyl, azlactone, acetyl, acetonyl, acetoacetyl, ester, isocyanato, epoxy, aziridinyl, acyl halide, and cyclic anhydride groups. Preferably the amine-reactive functional groups A are selected to react with the amine groups of the crosslinking agent at temperatures below about 50° C., preferably below 25° C. such that the reaction takes place during the coating and drying operation.

Representative azlactone group-substituted functional compounds of Formula V include: 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5]spirodec-1-ene-4-one; 2-ethenyl-5,6-dihydro-4H-1,3-oxazin-6-one; 2-ethenyl-4,5,6,7-tetrahydro-1,3-oxazepin-7-one; 2-isopropenyl-5,6-dihydro-5,5-di(2-methylphenyl)-4H-1,3-oxazin-6-one; 2-acryloyloxy-1,3-oxazolin-5-one; 2-(2-acryloyloxy)ethyl-4,4-dimethyl-1,3-oxazolin-5-one; 2-ethenyl-4,5-dihydro-6H-1,3-oxazin-6-one; and 2-ethenyl-4,5-dihydro-4,4-dimethyl-6H-1,3-oxazin-6-one.

Representative acetoacetyl group-substituted functional compounds of Formula V include 2-(acetoacetoxy)ethyl methacrylate.

Representative carboxyl group-substituted functional compounds of Formula V include (meth)acrylic acid, 3-(meth)acryloyloxy-propionic acid, 4-(meth)acryloyloxy-butyric acid, 2-(meth)acryloyloxy-benzoic acid, 3-(meth)acryloyloxy-5-methyl benzoic acid, 4-(meth)acryloyloxymethyl-benzoic acid, phthalic acid mono-[2-(meth)acryloyloxy-ethyl]ester, 2-butynoic acid, and 4-pentynoic acid.

Representative isocyanate group-substituted functional compounds of Formula V include 2-isocyanatoethyl(meth)acrylate, 3-isocyanatopropyl(meth)acrylate, 4-isocyanatocyclohexyl(meth)acrylate, 4-isocyanatostyrene, 2-methyl-2-propenyl isocyanate, 4-(2-(meth)acryloyloxyethoxycarbonylamino)phenylisocyanate, allyl 2-isocyanatoethylether, and 3-isocyanato-1-propene.

Representative epoxy group-substituted functional compounds of Formula V include glycidyl(meth)acrylate, thioglycidyl(meth)acrylate, 3-(2,3-epoxypropoxy)phenyl (meth)acrylate, 2-[4-(2,3-epoxypropoxy)phenyl]-2-(4-(meth)acryloyloxy-phenyl)propane, 4-(2,3-epoxypropoxy)cyclohexyl(meth)acrylate, 2,3-epoxycyclohexyl(meth)acrylate, and 3,4-epoxycyclohexyl(meth)acrylate.

Representative acyl halide group-substituted functional compounds of Formula V include (meth)acryloyl chloride, α-chloro(meth)acryloyl chloride, (meth)acryloyloxyacetyl chloride, 5-hexenoyl chloride, 2-(acryloyloxy) propionyl chloride, 3-(acryloylthioxy) propionyl chloride, and 3-(N-acryloyl-N-methylamino)propionyl chloride.

Other useful amine-reactive monomers include anhydride group-substituted functional monomers including maleic anhydride, (meth)acrylic anhydride, itaconic anhydride, 3-(meth)acryloyloxyphthalic anhydride, and 2-(meth)acryloxycyclohexanedicarboxylic acid anhydride.

The crosslinked copolymer layer may comprise one or more hydrophilic monomers which comprise at least one alkenyl group, preferably a (meth)acryloyl group, and a hydrophilic group, including poly(oxyalkylene) and ionic groups, for providing hydrophilicity to the substrate, or for providing greater selectivity to the substrate when binding biomaterials.

The hydrophilic groups may be neutral, have a positive charge, a negative charge, or a combination thereof. Useful neutral, hydrophilic comonomers include dimethylacrylamide, acrylamide, methacrylamide, hydroxyethyl(meth)acrylate, hydroxypropyl(meth)acrylate, N-vinylpyrrolidinone, N-vinylformamide, or combinations thereof.

In some embodiments, the hydrophilic monomer may have an acrylate group, or other ethylenically unsaturated groups, and a poly(alkylene oxide) group; e.g. monoacrylated poly(alkylene oxide) compounds, where the terminus is a hydroxy group or an alkyl ether group. Such monomers may be of the Formula VI:

$$CH_2{=}CR^1{-}C(O){-}X^1{-}(CH(R^1){-}CH_2{-}O)_n{-}R^1, \qquad VI$$

wherein each $R^1$ is independently H or $C_1$-$C_4$ alkyl,
$X^1$ is —O— or —$NR^1$—, and
n is 2 to 100.

Others include the alkenylazlactones adducts of polyetheramines (such as the monoamines based on the polyetheramine structure). One example of these compounds is the Jeffamine® series, from Huntsman, The Woodlands, Tex., USA.

Such hydrophilic comonomers are used in amounts of about 35 to about 97.5 parts by weight, preferably 60 to about 93 parts by weight, most preferably of about 70 to about 87 parts by weight, relative to 100 parts total monomer weight of the copolymer. However, when an ionic monomer is used as part of the hydrophilic comonomer component, it is used in amounts of 15 parts by weight or less, so as to not reduce the ability of the grafted substrate to interact with and capture similarly charged biological materials. In such an instance, the remainder of the hydrophilic comonomer component comprises a neutral comonomer.

Optionally, other comonomers may be included at low levels in the crosslinkable copolymer. These other comonomers may be selected from monomers well known in the art and commercially available, such as common (meth)acrylate esters, styrenes, vinyl ethers, and vinyl esters.

The functional copolymers, having photoinitiator groups and crosslinkable monomer groups may be prepared by a variety of free radical polymerization processes in which reactive monomers are copolymerized with comonomers. Typical solution polymerization processes have been reported, for example, in U.S. Pat. No. 4,304,705, (Heilmann et al. and U.S. Pat. No. 3,583,950, (Kollinsky et al.). The copolymer is prepared using a free-radical initiator, such as a thermal initiator, rather than a photoinitiator to avoid initiation of the photoinitiator monomer.

Prior to crosslinking the copolymer is of the formula:

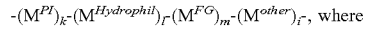

-$(M^{PI})_k$ are photoinitiator functional monomer units having "k" polymerized monomer units, where k is at least one
$(M^{Hydrophil})_l$ are hydrophilic monomer units having "l" polymerized monomer units,
$(M^{FG})_m$ are monomer units having amine-reactive functional groups and having "m" polymerized monomer units.
$(M^{other})$ represents other monomer units, having "i" polymerized monomer units, where "i" may be zero.

With reference to the amounts of the monomers:
k is 0.5 to 25 wt. % of the monomer units;
l is 35 to 97.5 wt. % of the monomer units;
m is 2-40 wt. % of the monomer units,
i is 0-20 wt. % of the monomer units,
based on 100 wt. % total monomers.

Once the appropriate copolymer (having crosslinkable functional groups, photoinitiator groups and hydrophilic groups) has been prepared, coating mixtures are formulated by adding crosslinkers or catalysts to the copolymer. This is conveniently done in an appropriate organic solvent that is nonreactive with functional groups of the copolymer. The copolymer may be diluted with solvent to a concentration of about 5% by weight or less prior to the addition of crosslinker or catalyst. In other embodiments, the copolymer may be diluted with solvent to concentrations of about 10% by weight or about 20% by weight prior to the addition of crosslinker or catalyst. The solvent used for dilution may be the same solvent in which the copolymer was prepared or may be one or more different solvents. Crosslinking time is conveniently controlled by copolymer concentration and the amount of crosslinker added, thereby allowing adequate time for coating, followed by rapid cure time to provide finished product. In general, the lower the copolymer concentration or the lower the amount of crosslinker, the longer it will take for the crosslinking to occur.

In embodiments wherein the copolymer comprises crosslinkable monomers such as alkenyl and (meth)acryloylalkyl silanes, or hydroxymethyl and alkoxymethyl(meth)acrylamides, crosslinking can be accomplished by methods well known in the art, such as by the addition of an acid catalyst.

With silane monomers having a hydrolysable group on silicon, adventitious water or the addition of a small amount of water may be helpful in generating the intermediate hydroxysilanes, ultimately leading to siloxane crosslinks. Acid catalyzed condensation of hydroxymethyl or alkoxymethyl acrylamide monomer units results in methylene crosslinks between polymer chains.

In some embodiments, the crosslinking agent for the copolymer is an amine functional compound having at least one primary amine groups and at least one other functional groups that is a) is reactive toward the amine-reactive functional group of the copolymer, or b) is self-crosslinking. Such compounds may be represented by the formula:

$$(HNR^1)_r\text{—}R^4\text{—}(FG)_q, \qquad \text{XIII}$$

where $R^1$ is H or $C_1$-$C_4$ alkyl,
$R^4$ is a (hetero)hydrocarbyl group, preferably a divalent alkylene group of 1 to 20 carbon atoms or a divalent poly(alkyleneoxy) group;
FG is a functional group that is a) is reactive toward the amine-reactive functional group of the copolymer, or b) is self-crosslinking, and subscripts r and q are at least one. These types of crosslinkers are described in detail in U.S. Pat. No. 6,794,458 (Haddad), the disclosures of which are incorporated herein.

In preferred embodiments the crosslinking agent is a polyamine: FG is of the formula
—$NHR^1$, where $R^1$ is H or $C_1$-$C_4$ alkyl to provide a crosslinking compound of the formula:

$$R^4(NHR^1)_m, \text{ where}$$

$R^4$ is a (hetero)alkylene group;
$R^1$ is H or $C_1$-$C_4$ alkyl, and at least one $R^1$ is H, and m is at least two.

Crosslinkers useful for the purposes of the present invention include, without limitation, materials that include nucleophilic groups that will undergo addition or substitution reactions with amine-reactive functional groups. Suitable crosslinkers include primary polyamines, such as ethylenediamine, 1,3-propanediamine, 1,3-diamino-2-hydroxypropane, 1,6-hexanediamine, tris-(2-aminoethyl)amine, and the like; and polyetherpolyamines, such as 4,7,10-trioxa-1,13-tridecanediamine, 3,6-dioxa-1,8-diaminooctane, amine-terminated polyethyleneglycol and polypropyleneglycol homopolymers and copolymers, and the like.

Another class of crosslinking agents includes primary/secondary (1°/2°) amine-containing compounds. In these materials, the primary amine provides rapid reaction with an azlactone group on the copolymer at room temperature, while the secondary amine is relatively slow to react. Removing the solvent, raising the temperature of the coated article, or both allows the secondary amine to react to form the crosslinked coating. Suitable primary/secondary amine-containing compounds include, without limitation, N-methyl-1,2-ethanediamine, N-ethyl-1,2-ethanediamine, N-isopropyl-1,2-ethanediamine, and other N-alkyldiaminoalkanes. Increasing the steric bulk of the N-alkyl substituent provides a greater barrier to reaction of the secondary amino group, thus necessitating a higher temperature to produce crosslinking.

Another class of crosslinkers that may be used for the purposes of the invention include aminoalkylalkoxysilanes such as, for example, 3-aminopropyltrimethoxysilane, 3-aminopropyltriethoxysilane, N-[3-(trimethoxysilyl)propyl]ethylenediamine, or other aminoalkylmono-, di- and tri-alkoxysilanes. The amino group undergoes a reaction with an amine-reactive functional group of the copolymer, providing a pendant alkoxysilane group on the copolymer. Upon dry-down, the alkoxy groups may be hydrolyzed and subsequently form siloxane crosslinks between polymer chains. Depending upon the nature of the substrate, covalent bonds may simultaneously be made with functional groups on the surface of the substrate (for example, if the substrate is siliceous, siloxane linkages to the substrate may be formed).

The stoichiometry between the amine groups of the crosslinker and the reactive functional groups of the copolymer can be less than 1:1 up to 1:1, preferably 0.1:1, more preferably 0.5:1 to 1:1 Thus, the amine-reactive functional group content in the original copolymer will provide an upper limit on the amount of crosslinker that may be added to the coating formulation. The primary purpose of the crosslinked coating is to provide the surface of the substrate with photoinitiator sites from which graft polymerization can take place. In some instances, a secondary purpose of the coating is to render the substrate surface more hydrophilic so as to reduce nonspecific binding of biological materials.

Ligand monomers useful for the purposes of the invention are functional monomers that comprise a free-radically polymerizable alkenyl or (meth)acryloyl group and a functional group that is either a ligand group capable of interacting with biological materials or a reactive group that can be utilized to attach a ligand group via an appropriate chemical reaction. Useful ligand monomers are functional monomers of Formula VIIIa or b.

$$Z^1\text{—}Y^2\text{—}X^1\text{—}CO\text{—}CR^1\!=\!CH_2 \qquad \text{(VIIIa), or}$$

$$Z^1\text{—}Y^2\text{—}CR^1\!=\!CH_2 \qquad \text{(VIIIb)}$$

wherein $X^1$ is —O— or —$NR^1$—, and $R^1$ is H or $C_1$-$C_4$ alkyl.

In Formulas VIII, group $Y^2$ is a linking group selected from a single bond or a (hetero)hydrocarbyl divalent group that contains an alkylene, heteroalkylene, arylene, or combination thereof. The group $Y^2$ can further contain other optional groups that function to connect two or more alkylenes, heteroalkylenes, arylenes, or mixtures thereof. The optional groups can include, for example, a carbonyl, carbonyloxy, carbonylthio, carbonylimino, oxy, thio, —$NR^1$—, where $R^1$ is H or $C_1$-$C_4$ alkyl, or combinations thereof Group $Z^1$ is a first ligand functional group selected from (1) an acidic group or a salt thereof, (2) an amino group or a salt thereof, (3) a guanidine or biguanide group or a salt thereof, (4) an azlactone group or a precursor to the azlactone group, (5) a glycidyl group, (6) a biological affinity ligand group, (7) a hydrophobic interaction group, (8) an isocyanate group, or (9) a combination thereof.

The functional ligand monomer of Formulas (VIII) has both an ethylenically unsaturated group capable of undergoing a free radical polymerization reaction plus a ligand functional group $Z^1$. The functional monomer of Formula (VIII) undergoes a free radical polymerization reaction with the PI-functionalized substrate resulting in the formation of a grafted substrate that includes a grafted chain extending from the solid support. In many embodiments, the solid support has multiple grafted chains. The grafted chain includes at least one, preferably two or more grafted monomer units of formulas VIIIa and/or b.

The group $Z^1$ of the ligand functional monomers of Formulas VIII can be an acidic group or a salt thereof, and are useful for the preparation of cation exchange substrates. The functional monomer can be a weak acid, a salt of a weak acid, a strong acid, a salt of a strong acid, or a combination thereof. The ligand functional monomer can be in a neutral state but capable of being negatively charged if the pH is adjusted. Some exemplary ligand functional monomers are sulfonic acids or salts thereof such as (meth)acrylamidosulfonic acids or salts thereof. More specific (meth)acrylamidosulfonic acids include, but are not limited to, (meth) acrylamidomethanesulfonic acid, 2-(meth) acrylamidoethanesulfonic acid, and 2-(meth)acrylamido-2-methylpropanesulfonic acid. Salts of these acidic monomer can also be used. Some other exemplary functional monomers having an acid group or salt thereof include other sulfonic acids such as vinylsulfonic acid, 3-sulfopropyl (meth)acrylate, sulfoethyl(meth)acrylate, and 4-styrenesulfonic acid.

Still other exemplary functional monomers having an acid group include, but are not limited to, phosphonic acids or salts thereof or carboxylic acids or salts thereof. For example, the function monomers can be (meth)acrylamidoalkylphosphonic acids such as 2-(meth)acrylamidoethylphosphonic acid and 3-(meth)acrylamidopropylphosphonic acid; acrylic acid and methacrylic acid; and carboxyalkyl (meth)acrylates such as 2-carboxyethyl(meth)acrylate and 3-carboxypropyl(meth)acrylate. Still other suitable monomers include (meth)acryloylamino acids, such as those described in U.S. Pat. No. 4,157,418 (Heilmann). Exemplary (meth)acryloylamino acids include, but are not limited to, N-(meth)acryloylglycine, N-(meth)acryloylaspartic acid, N-(meth)acryloyl-β-alanine, and N-(meth)acryloyl-2-methylalanine. Salts of any of these acidic monomers can also be used. If the functional monomer is in the form of a salt of a weak acid or a salt of a strong acid, the counter ion of these salts can be, but are not limited to, alkali metal ions, alkaline earth metal ions, ammonium ions, or tetraalkylammonium ions.

A second type of ligand functional monomer of Formulas VIII has an amino group or a salt thereof for $Z^1$, and are useful for the preparation of anion exchange substrates. The amino group or salt thereof can be a primary amino group, secondary amino group, tertiary amino group, or quaternary ammonium group. This type of functional monomer can be a weak base, a strong base, a salt of a weak base, a salt of a strong base, or a mixture thereof. The functional monomer can be in a neutral state but capable of being positively charged if the pH is adjusted. If the functional monomer is in the form of a salt, the counter ion can be, but is not limited to, a halide (e.g., chloride), a carboxylate (e.g., acetate or formate), nitrate, phosphate, sulfate, bisulfate, methyl sulfate, or hydroxide.

Some exemplary functional monomers having an amino group or salt thereof include amino (meth)acrylates or amino (meth)acrylamides (as well as quaternary ammonium salts thereof) as shown in Formula VIIIc:

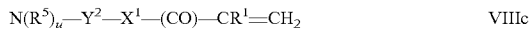

$$N(R^5)_u\text{—}Y^2\text{—}X^1\text{—(CO)—}CR^1\text{=}CH_2 \qquad \text{VIIIc}$$

wherein $X^1$ is —O— or —$NR^1$—, and $R^1$ is H or $C_1$-$C_4$ alkyl;

each $R^5$ is independently hydrogen, alkyl, hydroxyalkyl (i.e., an alkyl substituted with a hydroxy), aminoalkyl (i.e., an alkyl substituted with an amino), aryl, or aralkyl. The subscript u is equal to 2 for a primary, secondary, or tertiary amino group and equal to 3 for quaternary amino group. When u is equal to 3, the three $R^5$ groups are independently selected from alkyl, hydroxyalkyl, aminoalkyl, aryl, or arylalkyl. That is, $R^5$ typically is not equal to hydrogen when the variable u is equal to 3.

When the subscript u is equal to 2, the $R^5$ groups in Formula VIIIc taken together with the nitrogen atom to which they are attached can form a heterocyclic group that is aromatic, partially unsaturated (i.e., unsaturated but not aromatic), or saturated. Such a heterocyclic group can optionally be fused to a second ring that is aromatic (e.g., benzene), partially unsaturated (e.g., cyclohexene), or saturated (e.g., cyclohexane). The counter ions of the quaternary ammonium salts are often halides, sulfates, phosphates, nitrates, and the like.

In some embodiments of Formula VIIIc where the variable u is equal to 2, both $R^5$ groups are hydrogen. In other embodiments where the variable u is equal to 2, one $R^5$ group is hydrogen and the other is an alkyl having 1 to 10, 1 to 6, or 1 to 4 carbon atoms. In still other embodiments where the variable u is equal to 2, at least one of $R^5$ groups is a hydroxyl alkyl or an amino alkyl that has 2 to 10, 2 to 6, or 2 to 4 carbon atoms with the hydroxyl or amino group positioned on any of the carbon atoms of the alkyl group except the first. In still other embodiments where the variable u is equal to 2, at least one of the $R^5$ groups is an aryl having 5 or 6 carbon atoms; or an aralkyl with the alkyl group having 1 to 10 carbon atoms and the aryl group having 5 or 6 carbon atoms. In yet other embodiments, the two $R^5$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to, imidazolyl, piperazinyl, and morpholinyl. The heterocyclic group can be fused to an additional ring such as a benzene, cyclohexene, or cyclohexane. Exemplary heterocyclic groups fused to an additional ring include, but are not limited to, benzimidazolyl.

Exemplary amino (meth)acrylates of Formula VIIIc where $X^1$ is oxy include, but are not limited to, N,N-dialkylaminoalkyl(meth)acrylates such as, for example, N,N-dimethylaminoethyl(meth)acrylate, N,N-diethylaminoethyl(meth)acrylate, N,N-dimethylaminopropyl(meth)acrylate, N-tert-butylaminopropyl(meth)acrylate, and the like.

Exemplary amino (meth)acrylamides of Formula VIIIc where $X^1$ is —$NR^1$— include, but are not limited to, N-(3-aminopropyl)(meth)acrylamide, N-[3-(dimethylamino)propyl](meth)acrylamide, N-(3-imidazolylpropyl) (meth)acrylamide, N-(2-imidazolylethyl)(meth)acrylamide, N-(1,1-dimethyl-3-imidazoylpropyl)(meth)acrylamide, and N-(3-benzimidazolylpropyl)(meth)acrylamide.

Exemplary quaternary salts of the functional monomers of Formula VIIIc include, but are not limited to, (meth)acrylamidoalkyltrimethylammonium salts such as (meth)acrylamidopropyltrimethylammonium chloride; and (meth)acryloxyalkyltrimethylammonium salts such as 2-(meth) acryloxyethyltrimethylammonium chloride, and 2-(meth) acryloxyethyltrimethylammonium methyl sulfate.

A third type of functional monomer of Formulas VIIIa,b has a guanidine or biguanide or a salt thereof, and is useful for making anion exchange supports that are useful under conditions of high ionic strength.

A fourth type of functional monomer of Formulas VIIIa,b has an azlactone $Z^1$ group. Exemplary functional monomers having an azlactone group include, but are not limited to, vinyl alkylazlactones such as 2-vinyl-4,4-dimethylazlactone (also called 2-vinyl-4,4-dimethyl-2-oxazolin-5-one), 2-(4-vinylphenyl)-4,4-dimethylazlactone, 2-isopropenyl-4,4-dimethylazlactone, 2-vinyl-4-ethyl-4-methyl-2-oxazolin-5-one, and 2-vinyl-4,4-dimethyl-1,3-oxazin-6-one. A further embodiment of the fourth type of functional monomer has a precursor group of the azlactone group as the $Z^1$ group. The precursor group can be subjected to a ring closure reaction to form the azlactone group. Exemplary functional monomers that can provide this precursor group include, but are not limited to, N-acryloylmethylalanine.

A fifth type of functional monomer of Formulas VIIIa,b has a glycidyl as the $Z^1$ group. Exemplary monomers having a glycidyl group include, but are not limited to, glycidyl (meth)acrylate.

The fourth and fifth types of functional monomers, as well as monomers having an isocyanate group, such as 2-isocyanatoethyl(meth)acrylate, are useful, by virtue of their reactive functional groups, for the preparation of other types of supports, including immobilized enzyme supports, ion exchange supports, hydrophobic interaction supports, and biological affinity separation supports.

A sixth type of functional monomer of Formulas VIIIa,b has a hydrophobic $Z^1$ group, useful for the preparation of hydrophobic interaction supports.

Still other functional monomers have a combination of two or more functional $Z^1$ groups selected from (1) an acidic group or salt thereof, (2) an amino group or salt thereof, (3) a hydroxyl group, (4) an azlactone group, or (5) a glycidyl group. Exemplary functional monomers having multiple and different types of functional groups are 3-(meth)acryloxy-2-hydroxypropyltrimethylammonium chloride and 2-(meth)acrylamidoglycolic acid.

In some preferred embodiments, the crosslinked copolymer on the surface of the substrate comprises polymerized guanidinyl ligand-functional monomer units of the formulas:

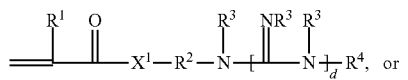

IXa

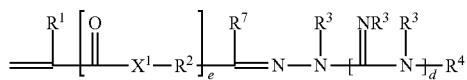

IXb wherein
$R^1$ is H or $C_1$-$C_4$ alkyl;
$R^2$ is a (hetero)hydrocarbyl group, preferably a divalent alkylene having 1 to 20 carbon atoms;
each $R^3$ is independently H or $C_1$-$C_4$ alkyl;
$R^4$ is H, $C_1$-$C_{12}$ alkyl or —N($R^3$)$_2$;
$R^7$ is H or hydrocarbyl, preferably $C_1$-$C_{12}$ alkyl or aryl;
$X^1$ is —O— or —NR$^3$—,
e is 0 or 1, and
d is 1 or 2.

Such ligand monomers of Formula IX a and b may be made by condensation of an alkenyl or alkenoyl compound, typically a (meth)acryloyl halide, a (meth)acryloylisocyanate, or an alkenylazlactone, with a compound of formulas Xa or Xb:

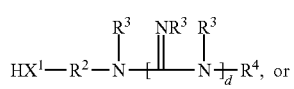

Xa

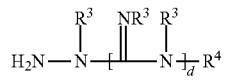

Xb where $X^1$, $R^2$ to $R^4$, and d are as previously defined.

Other ligand monomers may be made by condensation of a carbonyl containing monomer, such as acrolein, vinylmethylketone, diacetone acrylamide or acetoacetoxyethylmethacrylate, optionally in the presence of a reducing agent, with a compound of formulas Xa or Xb.

The ligand monomer will be grafted to the crosslinked copolymer via the residue of the photoinitiator so that the copolymer will have ligand groups (from monomers of the formulas VIIIa,b or IXa,b) attached thereto of the formula:

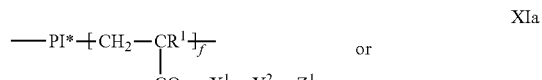

XIa

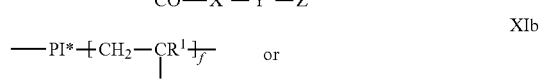

XIb

XIc

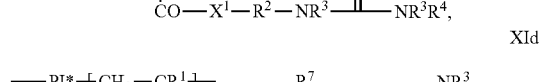

XId wherein
$R^1$ is H or $C_1$-$C_4$ alkyl;
$R^2$ is a (hetero)hydrocarbyl group, preferably a divalent alkylene having 1 to 20 carbon atoms;
each $R^3$ is independently H or $C_1$-$C_4$ alkyl;
$R^4$ is H, $C_1$-$C_{12}$ alkyl or —N($R^3$)$_2$;
$R^7$ is H or hydrocarbyl, preferably $C_1$-$C_{12}$ alkyl or aryl;
$X^1$ is —O— or —NR$^3$—,
$Y^2$ is a linking group selected from a single bond or a (hetero)hydrocarbyl divalent group; and
PI* is the residue of a photoinitiator grafted to the substrate surface.

With reference to the PI* group, a grafting photoinitiator monomer such as 2-propenoylamino-2,2-dimethylethanoic acid, 2-(4-(2-hydroxy-2 methylpropanoyl)phenoxy)ethyl ester may be incorporated into the crosslinked copolymer. In the presence of UV, the photoinitiator group undergoes alpha cleavage to two radicals. In the presence of the ligand monomer, or other monomers, the radical may add to the ethylenically unsaturated group (such as the depicted acryloyl group) to initiate polymerization of the ligand monomer via the residue of the photoinitiator as shown in formula XI and illustrated in Scheme I below. It will be further understood that the radical addition product of the ligand monomer may further copolymerize with additional ligand monomers and the other optional monomers to produce a grafted polymer having ligand groups pendent therefrom.

Scheme 1

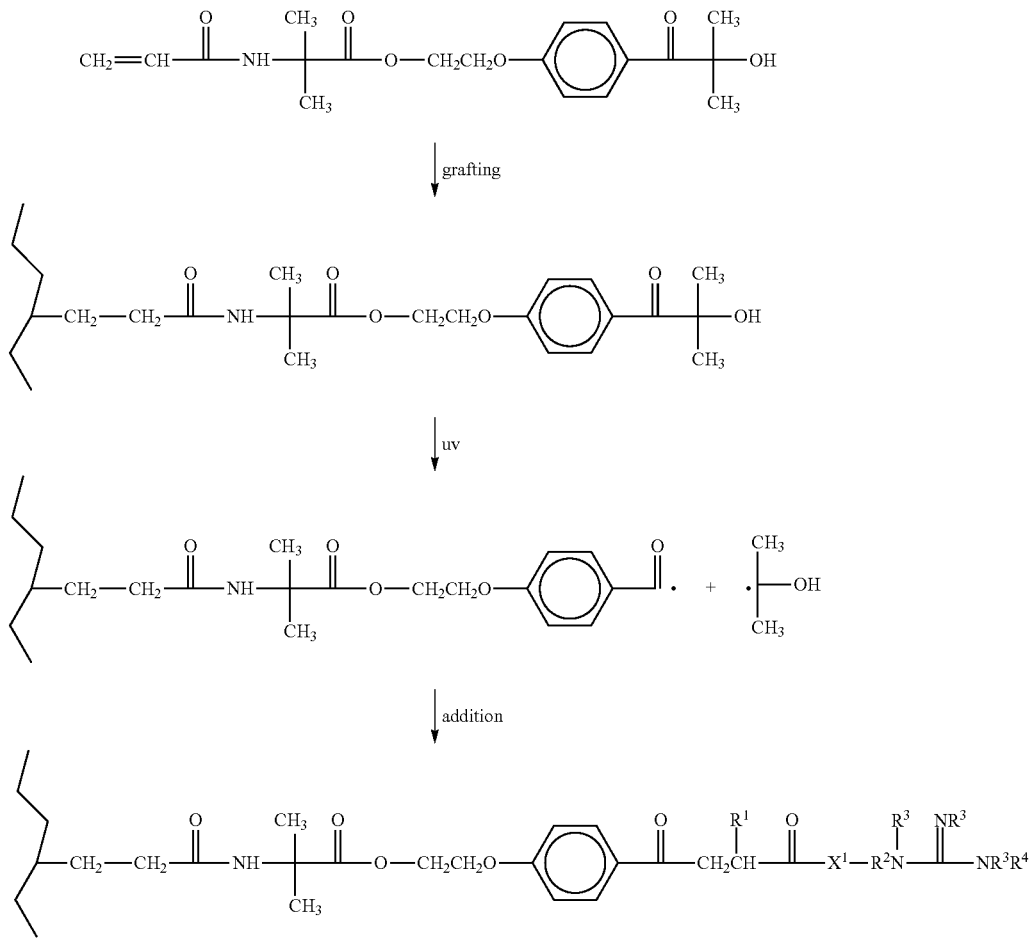

It will be further understood that the grafting process will yield a radical species, having a radical on the carbon alpha to the carbonyl of the ligand monomer of Formula I, that may further polymerize with one or more additional ligand monomers, one or more hydrophilic monomers and/or one of more crosslinking or "other" monomers, resulting in a grafted polymers having these groups pendent from the crosslinked copolymer chain as simply illustrated below. The formation of grafted polymer chains significantly increases the density of the desired ligand groups, and the efficiency of binding.

The resulting article comprises a substrate, and a crosslinked copolymer on the surface thereof, the copolymer having grafted polymerized ligand monomers, and may be represented by the formula:

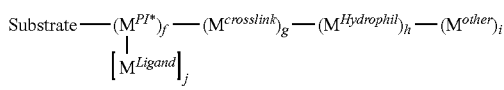

where $M^{PI*}$ represents the residue of the $M^{PI}$ monomer units having "f" polymerized monomer units, where f is at least one, $M^{crosslink}$ represent the monomer units derived from the $M^{FG}$ monomer units, having been subsequently functionalized with the amino-functional crosslinking agent, and having "g" polymerized monomer units, where g is at least one;

$M^{Hydrophil}$ represents hydrophilic monomer units having "h" polymerized monomer units, where h is at least one;

$M^{Ligand}$ represents ligand monomer units having "j" polymerized monomer units, where j is at least 1

$M^{other}$ represents other monomer units, having "i" polymerized monomer units, where "i" may be zero.

It will be understood that the values of the subscripts will correspond to the weight percents of each monomer unit as taught supra. It will be further understood that the depicted copolymer may further have $M^{PI*}$ monomer units unsubstituted by $M^{Ligand}$ monomer units, and may further have unsubstituted $M^{FG}$ monomer units.

It will be understood with respect to the above formula that the copolymer may be random or block, and that the pendent ligand monomer units may further comprise additional copolymerized monomer units, including hydrophilic monomer units, "other" monomer units and crosslinking monomer units.

The ligand functionalized substrates may be prepared using a combination of process steps. The method may comprise:

1) providing a base substrate, preferably a porous base substrate;
2) providing a coating solution comprising a copolymer of one or more monomers having a photoinitiator group, one or more monomers having an amine-reactive functional group, one or more hydrophilic monomers, one or more "other" monomers, and an amine-functional crosslinking agent;
3) coating the substrate with the coating solution;
4) crosslinking the coating on the surface of the substrate with the amine-functional crosslinking compound to produce a crosslinked copolymer;
5) drying the coated substrate;
6) imbibing the substrate bearing the crosslinked copolymer with a solution or suspension comprising (a) one or more ligand functional monomers, (b) optionally one or more hydrophilic monomers; and optionally c) one or more "other" monomers;
7) exposing the imbibed base substrate to UV radiation so as to generate free radicals from the photoinitiator groups of the copolymer, and
graft-polymerizing the ethylenically unsaturated, free-radically polymerizable groups of the monomers onto the surface of the base substrate.

In some embodiments, the imbibing solution comprises only the ligand functional monomer(s) and the solvent. In other embodiments, the imbibing solution comprises one or more "other" monomers. These other monomers include the same comonomers described for the crosslinked copolymer, including hydrophilic comonomers, but also include multifunctional (meth)acryloyl monomers, including (meth)acrylate and (meth)acrylamide monomers. These latter comonomers may be included to provide branching or a low degree of crosslinking to the grafted ligand functional polymer chains. Examples of useful multifunctional (meth)acrylates include, but are not limited to, di(meth)acrylates, tri(meth)acrylates, and tetra(meth)acrylates, such as ethyleneglycol di(meth)acrylate, 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, methylenebisacrylamide, ethylenebisacrylamide, hexamethylenebisacrylamide, diacryloylpiperazine, and mixtures thereof.

The solvent for the imbibing solution may be any solvent useful for conducting free radical polymerization processes. In many embodiments the solvent is water or a water/water-miscible organic solvent mixture. The ratio of water to organic solvent can vary widely, depending upon monomer solubility. With some monomers, it is typically greater than 1:1 (v/v) water to organic solvent, preferably greater than 5:1, and more preferably greater than 7:1. With other monomers, a higher proportion of organic solvent, even up to 100%, with some alcohols especially, may be preferred.

Any such water miscible organic solvent preferably has no groups that would retard the polymerization. In some embodiments, the water miscible solvents are protic group containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments higher glycols such as poly(ethylene glycol) may be used. Specific examples are methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and mixtures thereof.

In other embodiments, non-protic organic solvents that can also be used such as aliphatic esters and ketones and sulfoxides, ethyl acetate, methoxyethyl acetate, ethoxyethyl acetate, propoxyethyl acetate, butoxyethyl acetate, triethyl phosphate, acetone, methyl ethyl ketone, methyl propyl ketone and dimethyl sulfoxide.

The concentration of each component in the imbibing solution may vary depending on a number of factors including, but not limited to, the grafting monomer or monomers in the imbibing solution, the extent of grafting desired, the reactivity of the grafting monomer(s), and the solvent used. Typically, the total concentration of the monomers in the imbibing solution ranges from about 0.1 wt % to about 60 wt %, desirably, from about 1 wt % to about 35 wt %, more desirably, from about 5% to about 25%, based on a total weight of the imbibing solution. Following grafting, washing, and drying, typical total weight gains by the substrate are in the range of about 5% to about 30%, in the range of about 10% to about 25%, or in the range of about 12% to about 20%.

UV light sources can be relatively low light intensity sources such as blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers, or relatively high light intensity sources such as medium pressure mercury lamps which provide intensities generally greater than 10 mW/cm$^2$, preferably between 15 and 450 mW/cm$^2$. Where UV radiation is used to fully or partially polymerize the composition, moderate intensities and longer exposure times are preferred. For example, an intensity of about 10 to 50 mW/cm$^2$ and an exposure time of about 1 to 5 seconds may be used successfully. Alternatively, an exposure time of up to about 30 minutes may be used. A preferred UV source is the Quant 48™ UV Curing System from Quantum Technologies, Irvine, Calif.

Subsequent to the grafting steps the grafted substrate may be subjected to an optional washing/rinsing step, where the functionalized substrate is washed or rinsed one or more times in a rinse chamber to remove any unreacted monomers, solvent or other reaction by-products from the functionalized substrate. Typically, the functionalized substrate is washed or rinsed up to four times using a water rinse, a saline rinse, and optionally an alcohol rinse, a combination of water and alcohol rinses, and/or a solvent rinse (e.g., acetone, MEK, etc). When an alcohol rinse is used, the rinse may include one or more alcohols including, but not limited to, isopropanol, methanol, ethanol, or any other alcohol that is practical to use and an effective solvent for any residual monomer. In each rinse step, the functionalized substrate may pass through a rinse bath or a rinse spray.

In the optional drying step, the functionalized substrate is dried to remove any rinse solvent from the functionalized substrate. Typically, the functionalized substrate is dried in an oven having a relatively low oven temperature for a desired period of time (referred to herein as "oven dwell time"). Oven temperatures typically range from about 30° C. to about 120° C., while oven dwell times typically range from about 120 to about 600 seconds. Any conventional oven may be used in the optional drying step. Suitable ovens include, but are not limited to, convection ovens and recirculating air ovens.

In the above-described methods of making a functionalized substrate, any of the above-mentioned porous base substrates, grafting monomers, and reactants may be used to form a given functionalized substrate. The porous base substrate is often in the form of a porous membrane such as a microporous membrane, a nonwoven web, or porous fibers. In some embodiments, the porous base substrate comprises a microporous membrane formed by a solvent-induced phase separation (SIPS) method.

In one embodiment, the methods provide an article having a ligand functionalized coating covalently grafted on the surface thereof, the ligand functionalized coating comprising the UV polymerization reaction product of a one or more ligand monomers, one or more hydrophilic monomers, and one or more optional "other monomers", the free radical polymerization product being the result of free radical polymerization initiated by the grafted photoinitiator monomer units on the surface of the substrate.

The method of making a ligand functionalized substrate alters the original nature of the porous base substrate, as the grafted and UV polymerized species include a ligand group. The method enables the formation of ligand functionalized substrates having many of the advantages of a porous bases substrate (e.g., mechanical and thermal stability, porosity), but with enhanced affinity for biomolecules such as enzymes, proteins, carbohydrates, lipids, nucleic acids, host cell proteins, endotoxins, and microbes, resulting from the monomers and steps used to form a given functionalized substrate.

The porous substrates having a coating of ligand-functionalized polymer are particularly suited as filter media, for the selective binding and removal of target biological species including proteins, cells, cell debris, microbes, nucleic acids, and/or viruses from biological samples. The present disclosure further provides a method for the removal of target biological species from a biological sample by contacting the sample with the ligand polymer functionalized substrate as described herein. As used herein "target biological species" may include a contaminant or a species of interest.

The ligand functionalized substrate is useful for the purification of biological or other fluid samples comprising biologically derived species (biological species). Biological species include, but are not limited to, cells, cell debris, proteins, nucleic acids, endotoxins, and viruses.

In some embodiments, the biological species being removed from the fluid is the object of the purification. For example, a recombinant protein or enzyme may be prepared in cell culture or by fermentation, and the substrate can be used to capture the protein or enzyme as the first step in the purification process. In another example, the substrate may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid.

Significantly, some of the ligand functional substrates are useful under conditions of high salt concentration or high ionic strength, i.e., they are "salt tolerant". Guanidine or biguanide containing ligands are especially preferred because of their ability to maintain ionic interactions under these high ionic strength conditions.

The substrate may be in any form such as particles, fibers, films or sheets. Suitable particles include, but are not limited to, organic particles, inorganic particles, and porous and nonporous particles. Preferably the base substrate is porous. Suitable porous base substrates include, but are not limited to, porous particles, porous membranes, porous nonwoven webs, and porous fibers The substrate may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

In some embodiments, the thermoplastic polymer may be surface treated, such as by plasma discharge, to provide suitable functionality to the surface of the substrate. Surface treatment provides functional groups such as hydroxyl groups that can improve wetting by the coating or optional primer solution. One such useful plasma treatment is described in U.S. Pat. No. 7,125,603 (David et al.).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(iminoadipolyliminohexamethylene), poly(iminoadipolyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

The substrate may be in any form such as films or sheets. Preferably the base substrate is porous. Suitable porous base substrates include, but are not limited to, porous membranes, porous woven and nonwoven webs, and porous fibers.

A preferred substrate is a porous substrate that is a microporous membrane such as a solvent-induced phase separation (SIPS) membrane. In this embodiment the porous base substrate comprises a nylon microporous film or sheet, such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. Nos. 3,928,517, 4,707,265 (Knight et al.), and U.S. Pat. No. 5,458,782 (Hou et al.).

In another embodiment, the porous substrate is a thermally-induced phase separation (TIPS) membrane. These are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

In many embodiments, the base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of biological materials. The efficiency of binding other target molecules may confer different optimal ranges.

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by wet laid, carded, air laid, spunlaced, spunbonding or melt-blowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly dispersed meltblown fibers. Any of the non-woven webs may be made from a single type of fiber or two or more fibers that differ in the type of thermoplastic polymer and/or thickness.

Further details on the manufacturing method of nonwoven webs of this invention may be found in Wente, Superfine Thermoplastic Fibers, 48 INDUS. ENG. CHEM. 1342(1956), or in Wente et al., Manufacture Of Superfine Organic Fibers, (Naval Research Laboratories Report No. 4364, 1954).

If desired, efficiency of binding and capture may be improved by using a plurality of stacked, ligand-functionalized porous membranes as a filter element. Thus the present disclosure provides a filter element comprising one or more layers of the porous, ligand functionalized substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and nonwoven fleece structures); sintered materials such as polyolefins, metals, and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment there is provided a filter assembly comprising the filter elements and a filter housing. In a further embodiment, this invention relates to a method of biological species capture comprising the steps of:

a) providing the filter element comprising one of more layers of the ligand functionalized base substrate of this disclosure, and b) allowing a moving biological solution containing a target biological species to impinge upon the upstream surface of the filter element for a time sufficient to effect binding of the target species.

The present disclosure is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims

EXAMPLES

Test Methods

Static BSA Capacity Method for Functionalized Substrates

Functionalized substrates were analyzed for static binding capacity by rocking one disk of the substrate in a solution of the test analyte overnight. The disk was prepared by die-punching a 24-mm diameter disk from a sheet of the substrate. Each disk was placed in a 5 mL centrifuge tube with 4.5 mL of BSA (bovine serum albumin) challenge solution (Catalog #A-7906; Sigma Aldrich; St. Louis Mo.) at a concentration of about 3.0 mg/ml in 25 millimolar TRIS (tris(hydroxymethyl)aminomethane) buffer, pH 8.0. The tubes were capped, and tumbled overnight (typically 14 hours) on a rotating mixer. The supernatant solutions were analyzed using a UV-VIS spectrometer at 279 nm (with background correction applied at 325 nm). The static binding capacity for each substrate was determined by comparison to the absorption of the starting BSA solution, and results are reported in mg/mL as the average of three replicates.

Dynamic BSA Capacity Method for Functionalized Substrates

Functionalized substrates were analyzed for dynamic binding of proteins by a passing solution of the test analyte through a 6-layer stack of the substrate. The stack was prepared by die-punching 25-mm diameter disks from a sheet of the substrate and placing the stack in a 25 mm diameter holder attached to an AKTA chromatography system (GE Healthcare, NY). BSA was prepared at a concentration 1 mg/mL in 25 millimolar TRIS buffer containing 50 millimolar NaCl, pH 8.0. The BSA challenge solution was pumped through the substrate stack at a flow rate of 1 mL/min and the UV absorbance of the effluent was monitored at a wavelength of 280 nm. The dynamic binding capacity of the substrate was evaluated using standard chromatography techniques, and reported in mg/mL at 10% breakthrough.

Static IgG Capacity Method for Functionalized Substrates

Functionalized substrates were analyzed for static binding capacity by rocking one disk of the substrate in a solution of the test analyte overnight. The disk was prepared by die-punching a 24-mm diameter disk from a sheet of the substrate. Each disk was placed in a 5 mL centrifuge tube with 4.5 mL of IgG challenge solution (Equitech Bio, Kerrville, Tex.) at a concentration of about 4.0 mg/mL 50 mM acetate buffer with 40 mM NaCl at pH 4.5. The tubes were capped, and tumbled overnight (typically 14 hours) on a rotating mixer. The supernatant solutions were analyzed using a UV-VIS spectrometer at 280 nm (with background correction applied at 325 nm). The static binding capacity for each substrate was determined by comparison to the absorption of the starting IgG solution, and results are reported in mg/mL as the average of three replicates.

Materials

DMA—Dimethylacrylamide, Sigma-Aldrich, Milwaukee, Wis.
VDM—vinyldimethylazlactone, SNPE, Inc, Princeton, N.J.
VAZPIA—photoinitiator monomer, adduct of VDM and Irgacure 2959 (CIBA, Basil, Switzerland) prepared as described in Example 1 of U.S. Pat. No. 5,506,279
Toluene, VWR, West Chester, Pa.
VAZO 67, Sigma-Aldrich, Milwaukee, Wis.
Ethylenediamine, Sigma-Aldrich, Milwaukee, Wis.
IEM-AGM—adduct of isocyanatoethylmethacrylate and agmatine sulfate, nominally 90% pure by NMR), prepared as described in Example 99 of copending U.S. Ser. No. 13/353,413.
MBA—methylenebisacrylamide, Sigma-Aldrich, Milwaukee, Wis.
Isopropanol, VWR, West Chester, Pa.
IPA/DI water—1:1 ratio by volume of isopropanol and water
PEG-MA—PEG(400) monomethacrylate, Polysciences, Warrington, Pa.
Nylon 66 membrane—(single reinforced layer nylon three zone membrane, nominal pore size 1.8 μm, #080ZN from 3M Purification, Inc., Meridan, Conn.),
DAAm—diacetone acrylamide, Alfa Aesar, Ward Hill, Mass.
AG—aminoguanidine sulfate, Alfa Aesar, Ward Hill, Mass.
MAPTAC—[3-(methacryloylamino)propyl]-trimethylammonium chloride, 50% by weight aqueous solution, Sigma-Aldrich, Milwaukee, Wis.
PEI—Polyethylenimine, MW 70,000, 30% by weight aqueous solution, Cat#00618, Polysciences, Inc., Warrington, Pa.
BUDGE—butanediol diglycidyl ether, Sigma Aldrich, Milwaukee, Wis.
DADMAC—diallyldimethylammonium chloride, Sigma-Aldrich, Milwaukee, Wis.
AMPS-Na—sodium salt of 2-acrylamido-2-methyl-2-propane sulfonic acid, from Lubrizol, Wickliffe, Ohio Examples 1-5

Preparation of Crosslinkable Polymeric Photoinitiators

Crosslinkable polymeric photoinitiator compositions were prepared by mixing DMA, VDM, VAZPIA, in the amounts shown in Table 1 with toluene (120 grams) and VAZO 67 (2 grams) in 16 ounce glass bottles. Each mixture was purged with a slow stream of nitrogen gas for 15 minutes, and the bottles were sealed and tumbled in a water bath equilibrated to 60° C. for 24 hours to convert the monomer to polymer. The resulting polymeric solution was diluted to 20% solids by adding isopropanol (200 grams). IR and $^1$H-NMR analyses confirmed the formation of the polymer of Example 1 as poly(DMA/VDM/VAZPIA in a ratio of 78:20:2 w/w).

TABLE 1

| Example | DMA (grams) | VDM (grams) | VAZPIA (grams) | VAZPIA (wt % in polymer) |
|---|---|---|---|---|
| 1 | 62.4 | 16 | 1.6 | 2 |
| 2 | 61.6 | 16 | 2.4 | 3 |
| 3 | 60.8 | 16 | 3.2 | 4 |
| 4 | 60.0 | 16 | 4.0 | 5 |
| 5 | 56.0 | 16 | 8.0 | 10 |

Example 6-10

Primed Membranes

Primer solutions were each prepared by mixing solutions of ethylenediamine (25.7 microliters) in isopropanol (102 grams) with each of the polymeric solutions (5 grams) of Examples 1-5 for Examples 6-10, respectively. Primed membranes were prepared by dipping Nylon 66 membranes (approximately 10 cm×10 cm) into a primer solution and removing excess solution with a #14 wire-wound coating rod. The primed membranes were allowed to air dry at ambient temperature for at least 15 minutes.

Examples 11-18

Grafted Membranes

A 20% solids w/w grafting solution was prepared by dissolving IEM-AGM (13.33 grams) and MBA (0.12 gram) in a solution of IPA/DI water (46.55 grams). This solution (17.81 grams) was mixed with PEG-MA (1.43 grams) and IPA/DI water (5.76 grams) to provide a 14.25% solids coating solution. The primed membranes of Example 6 or 9 were placed on a sheet of polyester film. Approximately 4.5 mL of grafting solution was pipetted onto the top surface of the membrane, and allowed to soak for 2 minutes. A second sheet of polyester film was placed on top of the membrane and excess grafting solution was removed using a #14 wire-wound coating rod. The sandwich was irradiated using a blacklight UV source on each side for the time shown in Table 2. The grafted membranes then were each placed in 500 mL polyethylene bottles, the bottles were filled with deionized water and shaken for 30 minutes to wash off residual monomer or ungrafted polymer. The water was replaced with 50 millimolar sodium acetate, pH 4.5 and washed for 30 minutes, followed by another 30 minutes with deionized water. The membranes were removed from the bottles and allowed to dry. Examples 11-15 were grafted with the 14.25% coating solution while Examples 16-18 were grafted with the 20% solids solution. Irradiation times, priming polymer, and static BSA binding capacities are listed in Table 2.

TABLE 2

| Example | Irradiation Time (min) | Primed Membrane | StaticBSA Capacity (mg/mL) |
|---|---|---|---|
| 11 | 5 | Ex 6 | 52 |
| 12 | 10 | Ex 6 | 146 |
| 13 | 15 | Ex 6 | 145 |
| 14 | 20 | Ex 6 | 146 |
| 15 | 30 | Ex 6 | 141 |
| 16 | 5 | Ex 9 | 110 |
| 17 | 10 | Ex 9 | 106 |
| 18 | 15 | Ex 9 | 107 |

Examples 19-23

A 20% solids solution of IEM-AGM containing MBA was prepared in IPA/DI water as described in Examples 11-18. Coating solutions were prepared by mixing varying amounts of this solution with PEG(400)MA and IPA/DI water as shown in Table 3. Primed membranes from Example 6 were coated as described in Examples 11-15 and grafted by exposing to UV radiation for 15 minutes per side. The grafted membranes were washed as described above, dried, and evaluated for both static and dynamic BSA binding capacities with results in Table 3.

TABLE 3

| Ex | IEM-AGM solution (grams) | PEG-MA (grams) | IPA/water (grams) | Static Capacity (mg/mL) | Dynamic Capacity (mg/mL) |
|---|---|---|---|---|---|
| 19 | 2.50 | 0.25 | 2.25 | 79 | 45 |
| 20 | 3.75 | 0.375 | 0.875 | 129 | 62 |
| 21 | 3.125 | 0.187 | 1.688 | 115 | 62 |
| 22 | 2.5 | 0.05 | 2.45 | 94 | 48 |
| 23 | 3.75 | 0.075 | 1.175 | 132 | 67 |

Examples 24-28

Membranes were prepared as in Examples 19-23 except that the grafting solutions contained no MBA in the IEM-AGM solution. BSA capacities are shown in Table 4.

TABLE 4

| Ex | IEM-AGM solution (grams) | PEG-MA (grams) | IPA/water (grams) | Static Capacity (mg/mL) | Dynamic Capacity (mg/mL) |
|---|---|---|---|---|---|
| 24 | 2.50 | 0.25 | 2.25 | 70 | 41 |
| 25 | 3.75 | 0.375 | 0.875 | 89 | 35 |
| 26 | 3.125 | 0.187 | 1.688 | 87 | 56 |
| 27 | 2.5 | 0.05 | 2.45 | 69 | 41 |
| 28 | 3.75 | 0.075 | 1.175 | 84 | 52 |

Examples 29-36

Coating solutions were prepared as described in Examples 11-18 except using DAAm, MBA, and IPA/deionized water compositions and coated primed membranes of Examples 6 and 9 as shown in Table 5. The membranes were exposed on each side to UV radiation for 15 minutes as described above. The grafted membranes were placed in 500 mL polyethylene bottles. A 2.0 molar aminoguanidine solution (AG) solution, prepared by dissolving AG (49.2 grams) in deionized water (100 mL) and adding 0.2 mL of concentrated hydrochloric acid, was added to each bottle. The membranes were allowed to react with the AG solutions for 3 hours, then excess solution was poured off. The bottles were filled with deionized water and shaken for 30 minutes to wash off residual monomer or ungrafted polymer. The water was replaced with 50 millimolar sodium acetate, pH 4.5, and washed for 30 minutes, then washed another 30 minutes with deionized water, and then allowed to dry. The static BSA capacities are listed in Table 5.

TABLE 5

| Ex | Primed Membrane | DAAm (grams) | MBA (grams) | IPA/water (grams) | Static Capacity (mg/mL) |
|---|---|---|---|---|---|
| 29 | Ex 6 | 0.5 | 0.005 | 19.5 | 27 |
| 30 | Ex 6 | 1.0 | 0.01 | 19.0 | 100 |
| 31 | Ex 6 | 2.0 | 0.02 | 18.0 | 106 |
| 32 | Ex 6 | 4.0 | 0.04 | 16.0 | 106 |
| 33 | Ex 9 | 0.5 | 0.005 | 19.5 | 25 |
| 34 | Ex 9 | 1.0 | 0.01 | 19.0 | 87 |
| 35 | Ex 9 | 2.0 | 0.02 | 18.0 | 104 |
| 36 | Ex 9 | 4.0 | 0.04 | 16.0 | 152 |

Examples 37-39

Coating solutions were prepared by dissolving MAPTAC in deionized water to produce the % solids grafting solutions on the primed membranes prepared in the examples shown in Table 6. The solutions were coated onto the primed membranes, and exposed to UV radiation for 15 minutes per side to graft the MAPTAC to the membranes. The grafted membranes were placed in 500 mL polyethylene bottles that were filled with deionized water and shaken for 30 minutes to wash off residual monomer or ungrafted polymer. The water was replaced with 50 millimolar sodium acetate, pH 4.5, and washed for 30 minutes. The sodium acetate was replaced to deionized water wash another 30 minutes, then allow to dry. The primed membranes, % solids of the coating solution, and static BSA capacities are listed in Table 6.

TABLE 6

Static BSA capacities (mg/mL) of MAPTAC grafted membranes

| Example | Primed Membrane | MAPTAC % Solids | BSA Capacity (mg/mL) |
|---|---|---|---|
| 37 | Ex 7 | 10 | 16 |
| 38 | Ex 8 | 10 | 30 |
| 39 | Ex 10 | 10 | 60 |
| 40 | Ex 7 | 15 | 40 |
| 41 | Ex 8 | 15 | 60 |
| 42 | Ex 10 | 15 | 87 |

Example 43-44

PEI was diluted to 1.0% solids with isopropanol. A 50 gram portion of this solution was formulated with enough BUDGE to react with 5% of the amine groups of the PEI polymer. Primed membranes were prepared from Nylon 66 membranes as described in Examples 6-10. The primed membranes were then immersed in a polymeric solution of Example 5 further diluted to 1% with isopropanol, allowed to soak for 5 minutes, then removed and rinsed in fresh isopropanol, and allowed to air dry. These membranes were coated with 5% and 10% MAPTAC solutions, grafted, washed and dried as described in Example 37. Static BSA capacities are listed in Table 7.

TABLE 7

Static BSA capacities (mg/mL) of MAPTAC grafted membranes

| Example | MAPTAC % Solids | BSA Capacity (mg/mL) |
|---|---|---|
| 43 | 5 | 77 |
| 44 | 10 | 120 |

Examples 45-47

Primed membranes were prepared with PEI as described in Example 43, except they were immersed in a 1% solids solution in isopropanol of polymer 4, allowed to soak for 5 minutes, removed and rinsed in fresh isopropanol, and allowed to dry. These membranes were coated with MAPTAC solutions, grafted, and washed and dried as described in Example 37. BSA capacities are listed in Table 8.

TABLE 8

Static BSA capacities (mg/mL) of MAPTAC grafted membranes

| Example | MAPTAC Solids (%) | BSA Capacity (mg/mL) |
|---|---|---|
| 45 | 5 | 48 |
| 46 | 10 | 77 |
| 47 | 15 | 94 |

Examples 48-53

Primed nylon membranes (approximately 10 cm×10 cm) prepared as described in Example 10 were coated with aqueous solutions of DADMAC in deionized water with and without the addition of MBA (1% by weight based on the amount of DADMAC) as shown in Table 9. The coated membranes were grafted, washed and dried as described in Example 37. Static BSA capacities are listed in Table 9.

TABLE 9

BSA Static capacities (mg/mL) of DADMAC grafted membranes

| Example | DADMAC Solids (%) | MBA | BSA Capacity (mg/mL) |
|---|---|---|---|
| 48 | 30 | No | 37 |
| 49 | 40 | No | 85 |
| 50 | 60 | No | 106 |
| 51 | 30 | Yes | 70 |
| 52 | 40 | Yes | 98 |
| 53 | 60 | yes | 103 |

Example 54

A primed nylon membrane prepared as described in Example 10 was coated with a 15% solids aqueous solution of AMPS-Na in deionized water, grafted, washed and dried as described in Example 37. This membrane was tested for its static binding capacity for IgG, and found to have a capacity of 102 mg/mL.

What is claimed is:

1. A method for preparing a ligand-functionalized substrate comprising:
   a) providing a base substrate;
   b) providing a coating solution comprising a copolymer of one or more monomer units having a photoinitiator group, one or more monomer units having a crosslinkable functional group, one or more hydrophilic monomer units, and optionally one or more "other" monomer units;
   c) coating the base substrate with the coating solution;
   d) crosslinking the coating to produce a crosslinked copolymer;
   e) imbibing the substrate bearing the crosslinked copolymer with a solution or suspension comprising (a) one or more ligand functional monomers, (b) optionally one or more hydrophilic monomers; and optionally c) one or more "other" monomers;
   f) exposing the imbibed base substrate to UV radiation so as to generate free radicals from the photoinitiator groups of the copolymer, and
   g) graft-polymerizing the monomers of step e) onto the surface of the base substrate.

2. The method of claim 1, wherein the hydrophilic monomer units of the copolymer comprise one or more of poly(oxyalkylene) (meth)acryloyl monomer units, (meth)acrylamide monomer units, vinyl amide monomer units, and hydroxyalkyl(meth)acryloyl monomer units.

3. The method of claim 1, wherein the monomer units having a crosslinkable functional groups are derived from monomers of the formula:

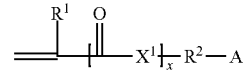

wherein
X$^1$ is —O— or —NR$^1$—,
R$^1$ is H or C$_1$-C$_4$ alkyl;
R$^2$ is a single bond or a (hetero)hydrocarbyl linking group,
A is an reactive functional group that is reactive with a crosslinking compound or is self-crosslinking; and
x is 0 or 1.

4. The method of claim 3 wherein A is an amine reactive functional group and is selected from carboxyl, oxazolinyl, azlactone, acetyl, acetonyl, acetoacetyl, ester, isocyanato, epoxy, aziridinyl, acyl halide, and cyclic anhydride groups.

5. The method of claim 1, wherein the monomer units having a crosslinkable functional groups are self crosslinkable and are derived from monomers selected from alkenyl or (meth)acryloyl silanes, hydroxymethyl(meth)acrylamides and alkoxymethyl(meth)acrylamides.

6. The method of claim 4, wherein the coating solution further comprises an amine functional crosslinking compound.

7. The method of claim 6 wherein the amine functional crosslinking compound is of the formula (HNR$^1$)$_r$—R$^4$-(FG)$_q$, where R$^1$ is H or C$_1$-C$_4$ alkyl,
R$^4$ is a (hetero)hydrocarbyl group;
FG is a functional group that is a) reactive toward the functional group of the copolymer, or b) self-crosslinking, and subscripts r and q are at least one.

8. The method of claim 7 wherein FG is —NHR$^1$, where R$^1$ is H or C$_1$-C$_4$ alkyl.

9. The method of claim 8 wherein the crosslinking compound is a polyamine of the formula R$^4$(NHR$^1$)$_m$, wherein R$^4$ is a (hetero)alkylene group;
R$^1$ is H or C$_1$-C$_4$ alkyl, and at least one R$^1$ is H, and m is at least two.

10. The method of claim 1 wherein the ligand functional monomers are of the formula:

Z$^1$—Y$^2$—X$^1$—CO—CR$^1$=CH$_2$, or

Z$^1$—Y$^2$—CR$^1$=CH$_2$ wherein X$^1$ is —O— or —NR$^1$—,
R$^1$ is H or C$_1$-C$_4$ alkyl,
Y$^2$ is a linking group selected from a single bond or a (hetero)hydrocarbyl divalent group;

$Z^1$ is a ligand functional group that binds biological species by ionic, covalent, hydrophobic, and biological affinity interactions.

11. The method of claim 1, wherein the ligand-functional monomer units are derived from monomers of the formulas:

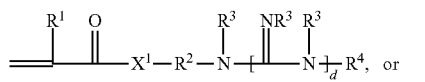  IXa

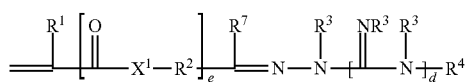  IXb wherein
$R^1$ is H or $C_1$-$C_4$ alkyl;
$R^2$ is a (hetero)hydrocarbyl group;
each $R^3$ is independently H or $C_1$-$C_4$ alkyl;
$R^4$ is H, $C_1$-$C_{12}$ alkyl or —N($R^3$)$_2$;
$R^7$ is H or hydrocarbyl, preferably $C_1$-$C_{12}$ alkyl or aryl;
$X^1$ is —O— or —N$R^3$—,
e is 0 or 1, and
d is 1 or 2.

12. The method of claim 1 wherein the monomers of the imbibing step e) comprises hydrophilic monomers.

13. The method of claim 1 wherein the monomers of the imbibing step e) comprises crosslinking monomers.

14. The method of claim 1 wherein the copolymer, prior to crosslinking, is of the formula:

-$(M^{PI})_k$-$(M^{Hydrophil})_l$-$(M^{FG})_m$-$(M^{other})_i$-, where $(M^{PI})_k$ are photoinitiator functional monomer units having "k" polymerized monomer units, where k is at least one $(M^{Hydrophil})_l$ are hydrophilic monomer units having "l" polymerized monomer units, $(M^{FG})_m$ are monomer units having crosslinkable functional groups and having "m" polymerized monomer units, $(M^{other})_i$ are other monomer units, having "i" polymerized monomer units, where "i" may be zero.

15. The method of claim 6 wherein stoichiometry between the amine groups of the crosslinker and the reactive functional groups of the copolymer is 0.1:1 to 1:1.

16. A ligand-functionalized substrate represented by the formula:

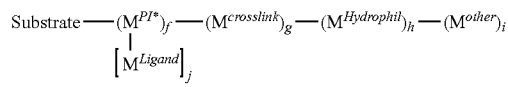

where
$M^{PI*}$ represents the residue of the $M^{PI}$ monomer units having "f" polymerized monomer units, where f is at least one,
$M^{crosslink}$ represent the monomer units derived from the $M^{FG}$ monomer units, having been subsequently crosslinked, and having "g" polymerized monomer units, where g is at least one and $(M^{FG})_m$ are crosslinkable monomer units;
$M^{Hydrophil}$ represents hydrophilic monomer units having "h" polymerized monomer units, where h may be zero;
$M^{Ligand}$ represents ligand monomer units having "j" polymerized monomer units, where "j" is at least 1
$M^{other}$ represents other (meth)acryloyl monomer units, where "i" may be zero.

* * * * *

UNITED STATES PATENT AND TRADEMARK OFFICE
CERTIFICATE OF CORRECTION

| | | |
|---|---|---|
| PATENT NO. | : 9,434,829 B2 | Page 1 of 1 |
| APPLICATION NO. | : 14/415862 | |
| DATED | : September 6, 2016 | |
| INVENTOR(S) | : Jerald Rasmussen | |

It is certified that error appears in the above-identified patent and that said Letters Patent is hereby corrected as shown below:

In the Specification

Column 4:
Line 40, delete "—$C_tH_{2t}O$—" and insert -- —$OC_tH_{2t}O$— --, thereof.

Column 7:
Line 57, delete "$CH_2+CR^1$" and insert -- $CH_2=CR^1$ --, thereof.

Column 10:
Line 44, after "thereof" insert -- . --.

Column 22:
Line 22, after "claims" insert -- . --.

Signed and Sealed this
Third Day of January, 2017

Michelle K. Lee
*Director of the United States Patent and Trademark Office*